United States Patent [19]

King et al.

[11] Patent Number: 5,723,319

[45] Date of Patent: Mar. 3, 1998

[54] CULTURED CELL LINE THAT INDUCIBLY EXPRESSES THE HEPATITIS B VIRUS GENOME, AND USES THEREOF FOR SCREENING ANTIVIRAL SUBSTANCES

[75] Inventors: Robert W. King, West Chester; Christopher S. Barker, Huntington Valley; Christoph Seeger, Melrose Park, all of Pa.

[73] Assignees: Avid Therapeutics, Inc.; Fox Chase Cancer Center, both of Philadelphia, Pa.

[21] Appl. No.: 462,216

[22] Filed: Jun. 5, 1995

[51] Int. Cl.$^6$ .............................. C12N 15/51; C12N 5/10; C12Q 1/70

[52] U.S. Cl. .............................. 435/69.3; 435/5; 435/7.1; 435/59; 435/70.1; 435/325

[58] Field of Search ............................ 435/5, 69.3, 325, 435/59, 7.1, 70.1

[56] References Cited

U.S. PATENT DOCUMENTS 5,026,635  6/1991  Ferguson et al. .......................... 435/5

OTHER PUBLICATIONS

Aoki–Sei et al., J. Inf. Dis. 164:843–851, 1991.
Brent et al., Cell 43:729–736, 1985.
Brown et al., Cell 49:603–612, 1987.
Carey et al., J. Mol. Biol. 209:423–432, 1989.
Cress et al., Science 251:87–90, 1991.
Deuschle et al., Proc. Natl. Acad. Sci. USA 86:5400–5404, 1989.
Dubendorff et al., J. Mol. Biol. 219:45–59, 1991.
Fuerst et al., Mol. Cell Biol. 7:2538–2544, 1987.
Fuerst et al., Proc. Natl. Acad. Sci. USA 83:8122–8126, 1986.
Gossen et al., Proc. Natl. Acad. Sci. USA 89:5547–5551, 1992.
Huang et al., Cell 27:245–255, 1981.
Jansen et al., Antimicrob. Agents and Chemoth. 37:441–447, 1993.
Korba et al., Antiviral Research 15:217–228, 1991.
Lee et al., Nature 294:228–232, 1981.
Ostrowski et al., Mol. Cell Biol. 3:2045–2057, 1983.
Sadowski et al., Nature 335:563–564, 1988.
Sells et al., Proc. Natl. Acad. Sci. USA 84:4641–4644, 1987.
Sells et al., Proc. Natl. Acad. Sci. USA 84:1005–1009, 1987.
Sells et al., J. Virol. 62:2836–2844, 1988.
Korba et al., Antiviral Res. 19:55–70, 1992.
Fields ED. Fundamental Virology, Second Edition 1990 Chapter 38 pp. 989–1021.Jan. 1, 1990.
Sells et al. 1987 PNAS USA 84 1005–1009, Jan. 1987.
Korba et al. 1991 Antiviral Research vol. 15 pp.217–228, Jan. 1991.
Gossen et al.1992 PNAS USA vol. 89 5547–5551, Jun. 1992.
Jansen et al. 1993 Antimicrobial Agents and Chemotherapy vol. 37 (3) 441–447, Mar. 1993.

Primary Examiner—Michael P. Woodward
Assistant Examiner—Mary K. Zeman
Attorney, Agent, or Firm—Dann, Dorfman, Herrell and Skillman

[57] ABSTRACT

Novel cell lines and methods are provided for inducibly expressing the Hepatitis B virus (HBV) genome within cultured cells. Cells are stably transformed with an HBV genome under control of an operator/promoter target sequence which can activate expression of the HBV genome when bound by a cognate transactivator protein. The cell lines are also stably transformed with a gene that encodes and expresses a suitable transactivator protein. Cells may be maintained under non-inducing conditions whereby the transactivator protein is unable to interact with the operator/promoter target sequence, so the HBV genome is not expressed. Under appropriate inducing conditions, the transactivator protein is enabled to interact with the operator/promoter target sequence, thereby activating expression of the HBV genome. The inducible system provides an effective and rapid cell-based assay to screen compounds for anti-hepadnaviral activity.

22 Claims, 4 Drawing Sheets

Fig. 1A
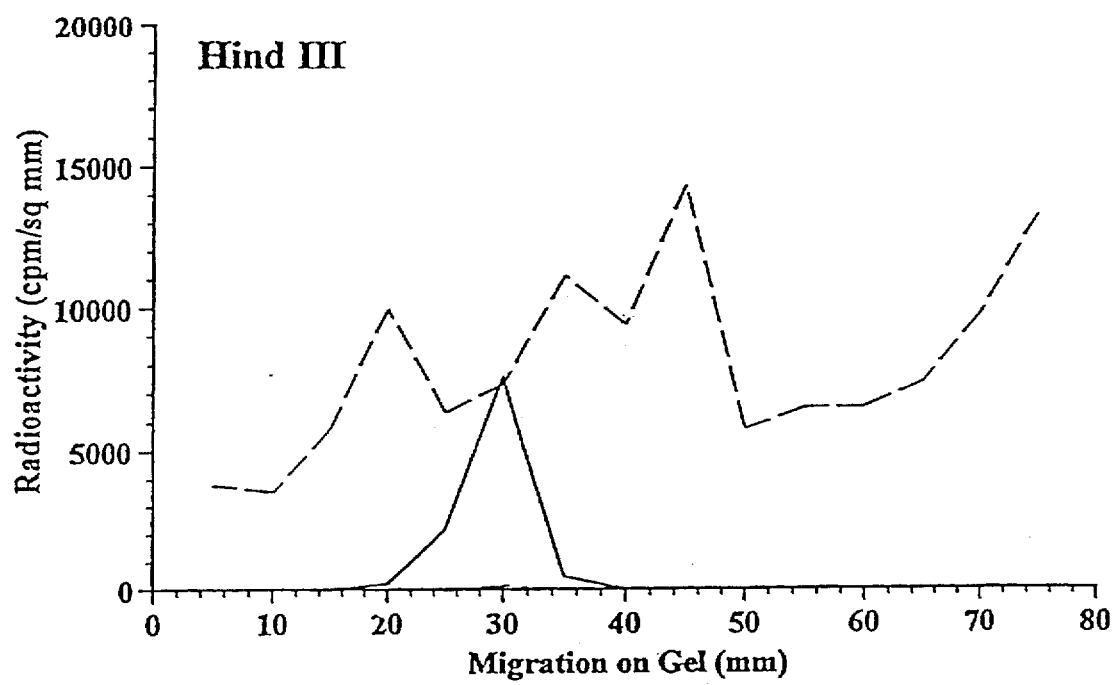
Fig. 1B
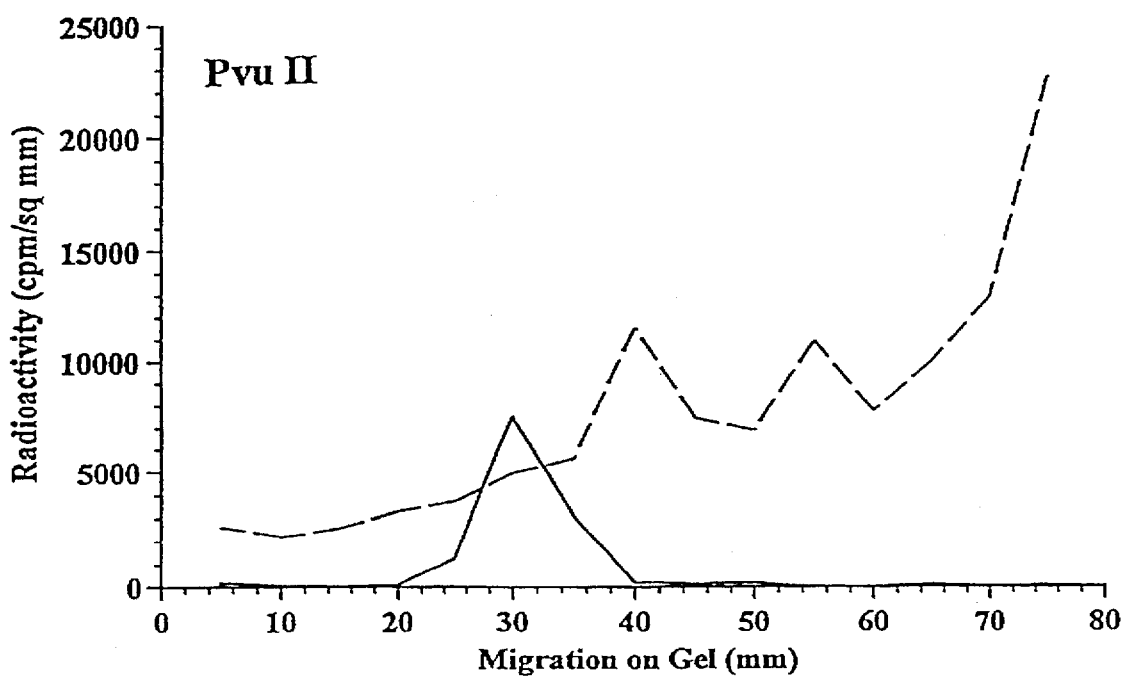
Figure 1

CULTURED CELL LINE THAT INDUCIBLY EXPRESSES THE HEPATITIS B VIRUS GENOME, AND USES THEREOF FOR SCREENING ANTIVIRAL SUBSTANCES

FIELD OF THE INVENTION

The present invention relates to assessment of pharmaceutical agents for antiviral activity against hepadnaviruses. In particular, this invention provides DNA constructs and novel cell lines for inducibly expressing the hepatitis B virus (HBV) genome. The inducible system provides an effective cell-based assay to screen compounds for anti-hepadnaviral activity.

BACKGROUND OF THE INVENTION

Hepatitis B virus infection is one of the most prevalent viral diseases in the world. The virus is known to cause both acute and chronic liver disorders. In addition, epidemiological studies have linked HBV infections with the formation of primary hepatocellular carcinomas.

Several types of regimens are currently available for treatment of individuals with chronic HBV infection, including, for example, the use of interferons and various nucleoside analogs. However, the protocols identified so far have been of only limited applicability. Some of the treatments reported have been found to be associated with moderate to serious side effects, while others are only transiently effective in suppressing HBV or are effective in only a small percentage of the population of HBV-infected individuals (See Tabor, pp 902–905 and Thomas, pp 817–822 Zuckerman, ed., A. R. Liss, Inc., New York, 1987). Thus, a need exists to identify other agents for treating HBV infection.

The development of other effective therapies against HBV infection will likely involve large-scale testing and screening of potential antiviral agents. A major obstacle to the rapid and simultaneous examination of large panels of candidate compounds is the time-consuming protocols involved in currently available cell-based testing system.

The current state of, the art for the detection of HBV in tissue culture is the HepG2 or 2.2.15 cell line assay (Korba & Milman, Antiviral Research 15: 217–228 1991). This assay uses HepG2 cells (a human hepatoblastoma cell line) stably transfected with DNA from a clone containing two tandemly arranged copies of the HBV genome. The resulting cell line (2.2.15 cells) secretes hepatitis B surface antigen particles, nucleocapsids and virions, which have been shown to elicit acute hepatitis in chimpanzees (Acs et al., Proc. Natl. Acad. Sci. USA 84: 4641–4644, 1988). The 2.2.15 cell line produces HBV at levels sufficient for measurement by conventional detection methods (Aoki-Sef et al., J. Infect. Dis. 164: 843–851 1988; Sells et al., Proc. Natl. Acad. Sci. USA 84: 4641–4644 1988).

Although the 2.2.15 cell assay offers the advantage of accurately modeling essential virologic features of chronic HBV infection, it is hampered by several disadvantages. Since the cell line is continuously producing HBV virions, the producing cells contain a stable pool of viral replicative intermediates. Before the effectiveness of any compound can be determined, the pool of replicative intermediates must be washed out from the test cells. The result of this wash out requirement is that the assay typically requires a minimum of 10 to 14 days for each individual compound. The determination of virus titer is further complicated since there is always some cell death during She course of the assay, resulting in release of replicative intermediates into the tissue culture medium. In addition, the use of these cells under the nonproliferative conditions needed to conduct the assay may not constitute the best culture system for cytotoxicity assessment. Nonproliferating cells, by definition, lack macromolecular synthesis. Therefore, this cell line, under the requisite assay conditions, is not suitable for assessing any potential antiviral compound that acts as a nonselective inhibitor of DNA synthesis.

Another disadvantage of the 2.2.15 cell line is that they are not amenable to large-scale screening. The level of production of HBV Dane particles in 2.2.15 cells is so low that large-scale screening of compounds for anti-HBV activity is not feasible.

In 1993, Jansen and co-workers developed an in vitro assay for the evaluation of anti-HBV compounds by a virion-specific polymerase chain reaction (PCR) assay (Jansen et al., Antimicrob. Agents and Chemotherapy 37: 441–447, 1993), The method combines basic immunological methods with conventional PCR technology. Fully-assembled viral particles are sequestered from cell culture samples by an antibody capture procedure. Isolated virions (free from viral intermediates) are then used as substrate for the amplification of HBV specific sequences in the presence of a biotinylated primer. Streptavidin is subsequently hybridized to the biotinylated PCR products, and viral titering is achieved spectro-photometrically. The use of the PCR technology confers sufficient sensitivity to detect very small amounts of DNA, allowing for testing of potential antiviral agents using proliferating cells. Therefore the method is suitable for testing nonselective inhibitors of DNA synthesis.

While the PCR-based method offers a considerable advantage over the nonproliferating 2.2.15 cell system, it is still disadvantaged by the lengthy growth period necessary to establish a culture ready for titration of extracellular virus. In addition, the method comprises a multistage quantitative analysis, introducing considerable opportunities for human and experimental errors, thus decreasing the reliability of the method.

The essential criteria for a useful testing system to evaluate the efficacy of antiviral agents are adequate and reliable sensitivity, ease of performance, low cost, and most of all, speed, to enable rapid testing of several compounds in a comparable fashion. A need exists for such a system, which heretofore has not been available.

SUMMARY OF THE INVENTION

The present invention provides novel cell lines and methods for inducibly expressing the HBV genome within cultured cells, and for utilizing the inducible expression system in cell-based assays for screening potential anti-hepadnaviral substances. According to one aspect of the invention, a cell line is provided which is capable of inducibly expressing a genome of hepatitis B virus. The cell line is stably transformed with a hepatitis B virus genome that is operably linked to a target nucleotide sequence for activating expression of the HBV genome. Activation of HBV genome expression is caused by interaction of the target sequence with a transactivator protein that specifically recognizes the sequence. The cell line is also stably transformed with a gene that encodes and expresses the transactivator protein. The transactivator protein is responsive to induction under a pre-determined inducing condition. Induction of the transactivator protein enables the protein to interact with the aforementioned target nucleotide sequence controlling expression of the HBV genome. This interaction activates expression of the HBV genome.

In a preferred embodiment of the invention, there is provided a human hepatic cell line that inducibly expresses a genome of human hepatitis B virus. The cell line is stably transformed with a human hepatitis B virus genome operably linked to a target nucleotide sequence for activating expression of the genome. The target sequence comprises at least one tet operator, operably disposed in the 5' direction from a minimal promoter, such as the cytomegalovirus early promoter. Activation of expression of the HBV genome is caused by interaction of the tet operator/CMV promoter target sequence with a transactivator protein that specifically recognizes and interacts with the target sequence. This cell line is also stably transformed with a gene that encodes and expresses the transactivator protein. The transactivator protein comprises a tetR/VP16 chimeric protein, which contains a tet operator-binding moiety and a VP16 activating moiety. The transactivator protein is responsive to induction by inducing conditions that comprise removal of tetracycline from culture media in which the cell line is maintained. This induction enables the transactivator protein to interact with the target tet/CMV nucleotide sequence, the interaction thereby activating expression of the human HBV genome.

In a particularly preferred embodiment, the cell lines described above are derived from the human hepatoma cell line, HepG2. An exemplary cell line of the invention is Hep AD38. "Hep AD38 was deposited with the American Type Culture Collection (ATCC) Apr. 1, 1996, under the reference number ATCC CRL 12077."

According to another aspect of the present invention, a method is provided for inducibly expressing a hepatitis B virus genome in a cultured mammalian cell line. In the method, a cell line is provided which is stably transformed with the HBV genome, operably linked to a target nucleotide sequence for activating expression of the genome. Activation of expression is caused by interaction between the target sequence and a transactivator protein that specifically recognizes and interacts with the target sequence. The cell line is also stably transformed with a gene that encodes and expresses the transactivator protein. The cell line is cultured in a nutrient medium under non-inducing conditions in which the transactivator protein is substantially prevented from interacting with the target nucleotide sequence; hence, the HBV genome is not expressed. The cell line is placed under inducing conditions that enable the transactivator protein to interact with the target nucleotide sequence, thereby activating expression of the HBV genome. The cell line is maintained under the inducing conditions for a pre-determined time to allow accumulation of products of expression of the HBV genome. The method may further comprise the step of detecting the presence or quantity of at least one of the HBV genome expression products.

According to another aspect of the invention, a cell-based assay is provided for screening potential anti-hepadnaviral agents. To perform the assay, a cultured cell line is utilized, which is stably transformed with a hepatitis B virus genome operably linked to a target nucleotide sequence for inducibly activating expression of the genome. The activation of HBV genome expression is caused by interaction between the target sequence and an inducible transactivator protein that specifically interacts with the target sequence. The cell line is also stably transformed with a gene that encodes and expresses the transactivator protein. The method comprises establishing at least one control sample and at least one test sample, each sample comprising a substantially equivalent number of cells from the cultured cell line, in a substantially equivalent volume of culture fluid. The test sample is exposed to a potential anti-hepadnaviral agent, then the cell lines comprising the control sample and the test sample are cultured in a nutrient medium under non-inducing conditions in which the transactivator protein is substantially prevented from interacting with the target nucleotide sequence. The cell lines of the control sample and test sample are then placed under inducing conditions that enable the transactivator protein to interact with the target nucleotide sequence, thereby activating expression of the HBV genome. Products of expression of the HBV genome are detected in each of the control sample and the test sample, and the presence or quantity of these products are compared between the control sample and the test sample. A difference between the control sample and the test sample is attributed to exposure of the test sample to the potential anti-hepadnaviral agent.

A preferred cell line to be used in each of the aforementioned methods is Hep AD38. Hep AD38 is a HepG2 derivative which has been stably transformed with human HBV genome operably linked to a tet operator/CMV promoter, as described above. The Cell line has also been stably transformed with a gene that encodes and expresses a tetR/VP16 transactivator protein, which specifically recognizes the tet operator/CMV promoter and activates expression of the HBV genome by interaction with the promoter. The tetR/VP16 transactivator is induced by removing tetracycline from the culture medium.

The cell lines and methods of the present invention provide a unique and advantageous testing system to evaluate the efficacy of anti-hepadnaviral agents. The inducible system provides a reliable and controllable cell-based assay for anti-HBV agents, which is also decidedly more rapid than other cell-based assay systems currently available for analysis of such agents.

BRIEF DESCRIPTION OF THE DRAWINGS

FIG. 1. Restriction endonuclease digests of genomic DNA isolated from 2.2.15 cells, HepG2 cells and Hep AD38 cells. Genomic DNA was digested with Hind III or Pvu II, separated by electrophoresis on a 1% agarose gel and probed for the presence of the HBV genome with a radioactively labeled probe specific for the HBV genome. FIG. 1A shows the Hind III digestion; FIG. 1B shows the Pvu II digestion.

DETAILED DESCRIPTION OF THE INVENTION

Figure 2:
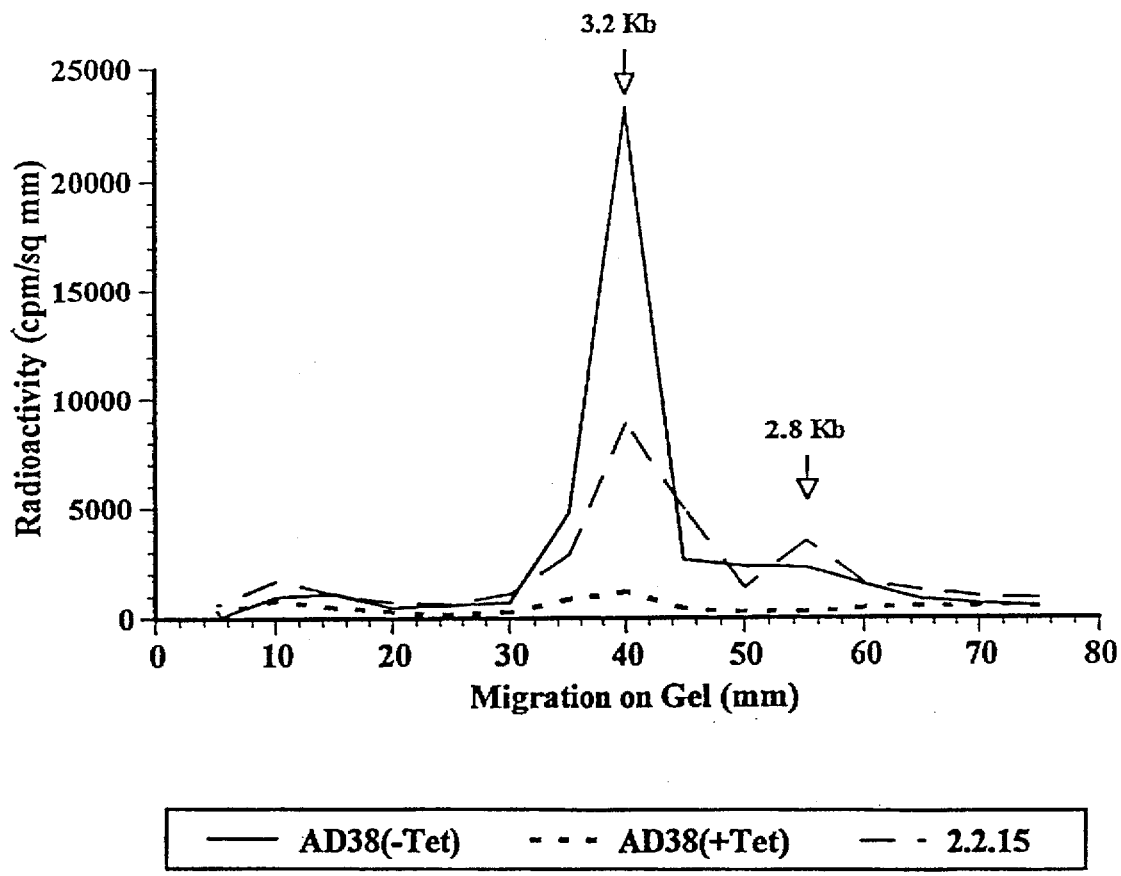
FIG. 2. Analysis of cells for HBV covalently closed circular DNA. DNA from Hep AD38 (induced), Hep AD38 (uninduced) and 2.2.15 cells were separated by electrophoresis on a 1% agarose gel and probed for the presence of the HBV genome sequences with a radioactively labeled probe.

The present invention expands upon an inducible promoter system originally described by Gossen and Bujard (Proc. Natl. Acad. Sci. USA, 89: 5547-5551, 1992). In that system, a procaryotic tet repressor was fused with the activating domain of virion protein 16 (VP16) of herpes simplex virus to form a eucaryotic tetracycline-controlled transactivator (tTA) that could be constitutively expressed in HeLa cells. A second construct was made in which the tetracycline operator (tetO) was placed 5' to the cytomegalovirus early promoter (eCMV) to facilitate binding of the tetracyline transactivator to the promoter element. The promoter was placed upstream of an indicator gens (encoding luciferass) to control and activate its expression. When both plasmids were introduced into the same mammalian cell, the expression of the luciferass gens was regulated by the presence or absence of tetracycline in the tissue culture medium. When tetracycline was present, the VP16-responsive promoter was repressed, due to binding of the tet repressor/VP16 chimetic protein to tetracycline, which prevents activation of the CMV promotor by the VP16 moiety. Removal of tetracycline from the medium enabled VP16 to bind to the CMV promotor, thereby inducing transcription of the indicator gene. Up to a 5-log induction was observed in this single-gene inducible system.

In accordance with the present invention, there are provided DNA constructs and stably-transfected human cell lines that utilize a dual-plasmid system for inducible expression, not simply of a single gene, but of the entire hepatitis B virus genome. The constructs and cell lines of the present invention represent a departure from the methodology described above, inasmuch as that method describes only the induction of a single reporter gene. Expression of an entire viral genome is significantly more complex than expression of a single gene. In the case of hepatitis B virus, HBV virions contain a partially double stranded DNA genome approximately 3200 bases in length. Upon entry of the virion into the cell, the genome is copied to a relaxed circular DNA, then converted to covalently closed circular DNA (cccDNA). The cccDNA serves as the template for synthesis of both pregenomic and subgenomic RNAs from which are translated the S (surface), C (core), P (polymerase) and X proteins. Following transcription and translation, the pregenomic RNA serves as template for reverse transcription into DNA by the viral P protein. The P and C proteins bind to a hairpin structure (epsilon) located at the 5' end of the pregenomic RNA that serves as both a packaging signal and as the site for initiation of minus strand DNA synthesis. DNA synthesis takes place within the newly formed viral capsid in the cytoplasm of the infected cell. The P protein serves as the primer for initiation of DNA synthesis and is covalently attached to the 5' end of the minus strand DNA. The polymerase containing the attached minus strand DNA translocates to a complementary sequence located at the 3' end of the pregenomic RNA and DNA synthesis continues. Simultaneous with minus strand DNA synthesis, a ribonuclease H function of the P protein degrades the pregenomic RNA from the RNA-DNA hybrid. Plus strand DNA synthesis is initiated near the 5' end of the minus strand DNA and requires a template switch to the 3' end in order for synthesis of relaxed circular DNA. Upon completion of DNA synthesis, the mature core particles become associated with internal cellular membranes which contain vital surface glycoproteins. Enveloped viral particles are formed by budding at the membrane and are released into the extracellular environment by the vesicular transport pathway.

As exemplified by HBV, then, it is clear that expression of an entire viral genome or of multiple genes within a cell comprises a complex series of events not generally associated with expression of a single gene. Prior to the discoveries made in accordance with the present invention, tetracycline-regulated expression of an entire viral genome or multiple gene products within a cell had not been reported, insofar as is known.

In accordance with the present invention, it has now been discovered that an inducible system, such as the Gossen/Bujard tetracycline transactivator plasmid system, can be utilized to achieve tight control of expression of the entire HBV genome. The engineered cell lines are such that the expression of HBV can be either completely inactivated or fine-tuned to reach a target virus titer. This system allows for the assessment of the efficiency of a given antiviral compound as distinct from unrelated host cell cytotoxicity, and without entailing elaborate and time-consuming setup and wash-out protocols. In this system, mammalian cells are transformed with two plasmid constructs. In a preferred embodiment, the first plasmid encodes a hybrid transactivator, such as that described by Gossen and Bujard, which comprises the amino terminal portion of the tetracycline (tet) repressor and the herpes simplex virus gene product 16 (VP16) at the carboxyl terminus. The second plasmid contains sequences corresponding to the HBV genome under control of at least one tet operator situated upstream of the human cytomegalovirus early promoter (eCMV). The tet operator/eCMV promoter is recognized, bound and activated by the tetR/VP16 transactivator. Thus, the presence of both constructs within a single cell enables the expression of HBV to be regulated by the presence or absence of tetracycline in the tissue culture medium, as described above.

The detailed description set forth below describes preferred methods for making and using the DNA constructs and cell lines of the present invention, and for practicing the methods of the invention. Any molecular cloning or recombinant DNA techniques not specifically described are carried out by standard methods, as generally set forth, for example, in Sambrook et al., "DNA Cloning, A Laboratory Manual," Cold Spring Harbor Laboratory, 1989.

I. Methods for Constructing Plasmids and Producing Human Cells Lines that Inducibly Express the HBV Genome The inducible HBV cell-based system is prepared according to the general methods set forth below for plasmid construction, transformation of cultured cells, and maintenance of cell lines.

A. Plasmids

As discussed above, the inducible system of the present invention relies on transforming cultured cells with two different plasmids. One plasmid encodes and constitutively expresses a transactivator protein capable of recognizing a target promoter sequence and activating expression of genes under control of that promoter. This plasmid is referred to herein generally as the "transactivator plasmid." The second plasmid comprises the HBV genome under control of the target promoter sequence recognized and activated by the transactivator protein (e.g., the tet operator/eCMV target sequence described above). This plasmid is referred to generally as the "HBV plasmid." A coding region (such as the HBV genome), arranged such that its expression is under control of (i.e., activatable/repressible by) a promoter/operator sequence, is sometimes said herein to be "operably linked" to the operator/promoter. The terms "operably linked" or "operably disposed" are used herein to mean that the respective promoter, operator and coding sequences, as well as any other 5' and 3' regulatory sequences, are arranged in the appropriate location, order and reading frame such that the desired control (e.g., expression) is effected under appropriate conditions.

Several transactivator/promoter pairs are known in the art and can be used to produce the transactivator plasmids and HBV plasmids of the invention. In a preferred embodiment, the transactivator is that described by Gossen and Bujard, and comprises tet repressor sequences fused to VP16 activator sequences. Particularly preferred is plasmid pUHD15-1 Neo, which contains the tet repressor-VP16 chimeric gene and a neomycin resistance gene (see Example 1). The HBV plasmid in this system comprises HBV sequences operatively linked to the tet operator, which has been modified to be responsive to the VP16 activator by inclusion of a minimal promoter. An exemplary HBV plasmid is ptetHBV (described in Example 1), which comprises the tet operator 5' to the eCMV promoter and human HBV genome. Expression of HBV is repressed as long as tetracycline is maintained in the cell culture medium. Upon removal of tetracycline, the transactivator becomes free to bind its cognate operator/promoter, which induces expression of the HBV genome. Construction of plasmids to be used in the tetracycline transactivator system is described in detail in Example 1.

Other activator/promoter sequences known in the art may also be used in construction of transactivator plasmids and HBV plasmids in accordance with the present invention. These include, but are not limited to: (1) the T7 lac promoter construct activated by T7 RNA polymerase as the transactivator (Dubendorfs & Studier, J. Mol. Biol., 219: 45–49, 1991); (2) the Lex A (binding domain)/Ga14 transcriptional activator-for the Lex A promoter (Brent & Ptashne, Cell 43: 729–736, 1985); (3) Ga14/VP16 (Carey et al., J- Mol. Biol. 209: 423–432, 1989; Cress et al., Science, 251: 87–90, 1991; Sadowski et al. Nature, 335: 563–564, 1988); (4) lac operator/repressor system as modified for eukaryotic expression (Brown et al., Cell 49: 603–612, 1987); (5) T7 polymerase-vaccinia virus promoter system (Fuerst et al., Proc. Natl. Acad. Sci. USA 83: 8122–8126; Fuerst et al., Molec. Cell Biol. 7: 2538–2544, 1987); (6) the T3 lac constructs activated by T3 RNA polymerase as the transactivator (Deuschle et al., Proc. Natl. Acad. Sci. USA 86: 5400–5404, 1989); and (7) glucocorticoid inducible mouse mammary tumor virus promoter system, (Lee et al., Nature 294: 228–232, 1981; Huang et al., Cell 27: 245–256, 1981; Ostrowski et al., Mol Cell. Biol. 3: 2045–2057, 1983). The tet operator/eCMV promoter exemplified herein also may be modified to comprise the vaccinia virus promoter (Fuerst et al., 1987, supra) instead of the eCMV promoter.

Cells transfected with the transactivator plasmid and/or the HBV plasmid can be selected by detecting the presence and accumulation of the gene products encoded by the respective plasmids. However, in a preferred embodiment, the plasmids are engineered to contain an additional selection mechanism. For example, the Gossen/Bujard tetracycline transactivator plasmid (pUHD15-1 Neo), which is particularly preferred for use in the present invention, comprises the Neo gene that encodes resistance to neomycin and related antibiotics. As another example, the HBV plasmid described in the Examples (ptet HBV) may be modified to also comprise a hygromycin resistance gene, such that cells transfected with the plasmid can be selected by their ability to grow on hygromycin-containing medium. In an alternative embodiment, a separate plasmid may be constructed that comprises an antibiotic resistance gene, and can be used to co-transfect cells. Persons skilled in the art will appreciate that a variety of genes encoding antibiotic resistance are available, and can be utilized in accordance with the present invention in the assembly of the transactivator plasmid and/or the HBV plasmid.

In a preferred embodiment, an additional plasmid is also utilized as a control in the assays described hereinbelow to determine the effects of potential anti-viral compounds on HBV expressed in the cells. The control plasmid is constructed in a manner similar to the HBV plasmid, but substituting an indicator gene for the HBV genome. In a particularly preferred embodiment, the lac Z gene from the bacterial lactose operon is utilized for this purpose. A second cell line is produced which contains the transactivator plasmid along with the control plasmid. This cell line is treated in the assays described hereinbelow as a negative control, to assure that any effects observed are due to the action of the compound being tested on HBV, and not on the transactivator protein.

B. Cell lines

The cell lines of the invention preferably are stable human cell lines that support production of hepadnaviral components. Cell lines useful for practice of the invention include, but are not limited to HepG2, an immortalized hepatic cell line (U.S. Pat. No. 4,393,133 to Knowles et al.), HuH7 ( a hepatic cell line); "293" cells (a human embryonic kidney cell line useful for transfection) and HeLa cells (a cervical carcinoma cell line utilized by Gossen and Bujard, 1992, supra). In accordance with the present invention, it has been found that HepG2 cells are more amenable to stable transfection than are other of the above-listed cell lines.

To achieve stable gene transfer, plasmid DNA must first be introduced into the host cells. This may be accomplished according to numerous methods known in the art, including, but not limited to: (1) calcium phosphate transfection; (2) transfection with DEAE-dextran; (3) electroporation; and (4) liposome-mediated transfection. For general protocols, see, e.g., chapter 9 in Current Protocols in Molecular Biology, Ausubel et al. (editors), John Wiley & Sons, Inc. 1987–1995. For stable transfer of genes into mammalian cells, the liposome-mediated transfection method is preferred in the present invention because of the large amount of DNA that can be introduced into the cells, thereby increasing the possibility of integration of the DNA into the host genome.

In accordance with the present invention, cell lines can be generated by co-transfection with the transactivator plasmid and the HBV plasmid (or the control plasmid), as described in detail in Example 1. Alternatively, a sequential transfection can be performed, whereby a first cell line is generated that has a genome containing a stably incorporated transactivator-encoding DNA sequence. That cell line is thereafter transfected with the HBV plasmid or a control plasmid to produce the cell lines of the invention.

Stable transfectants are selected by the ability of an individual cell colony to grow in the presence of a selected antibiotic, by virtue of a resistance-encoding gene carried on the transfecting plasmid DNA and incorporated into the genome of the cell. In a preferred embodiment as described above, both the transactivator plasmid and the HBV plasmid (or control plasmid) comprise a selectable marker gene for double selection of stable transfectants by antibiotic resistance.

Detection and quantitation of expression of the HBV genome in stably-transfected cell lines of the invention can be accomplished by a variety of known assays. For instance, as described in detail in Example 1, 2, 6 and 8, cells stably transfected with the HBV genome are grown in the appropriate medium for a selected period of time, then the medium is collected and analyzed for the presence of HBV DNA by dot blot hybridization or by conventional Southern hybridization, using a radioactively labeled probe having HBV DNA complementary sequences.

Several assays are available for quantitation of expressed HBV DNA in various stages of the HBV replication/life cycle. For example, an assay for HBV Dane particles may be employed, as described in Example 3. In particularly preferred embodiments, induced cell lines are assayed for the presence of infective virions of HBV. This may be accomplished by preparation and quantitation of viral core DNA produced by expression of stably integrated HBV genomes, as described in detail in Example 2. Alternatively, the presence and quantity of other replicative intermediates, such as covalently closed circular viral DNA (cccDNA), relaxed circular viral DNA, partially double stranded viral DNA and single stranded viral DNA, may be evaluated as described in Example 2. Additionally, standard procedures may be employed to detect and quantitate viral pregenomic or messenger RNA and viral proteins.

Using the assays described above, stably-transfected cell lines can be selected which possess optimum characteristics for use in cell-based assays of potential anti-viral compounds. Such cell lines are inducible within the range of 5–50 fold, and can be adjusted within that range to a selected level of induction, simply be varying the induction conditions, for instance, by varying tetracycline-mediated induction by maintaining a low concentration (e.g., up to 0.03 µg/ml) of tetracycline in a tetracycline induction system, and/or by varying the amount of time between induction of expression and collection of media for analysis. In addition, the HBV virions produced by expression of the HBV genome in the transfected cells should exhibit a dose-dependent response to known anti-hepadnaviral agents, such as those described in Example 5.

C. Exemplary Cell Lines

An exemplary cell line of the present invention is a HepG2 derivative referred to as "Hep AD38." The Hep AD38 cell line was created by co-transfecting HepG2 cells with plasmids, pUHD-15 and ptetHBV (see Example 1). It is a stably transfected cell line containing one copy of the human HBV genome that is integrated into the host cell genome. The human HBV genome is under the control of the tetracycline operator modified to be activatable by the tetR/VP16 transactivator by inclusion of the cytomegalovirus early promoter. Growth of this cell line in tissue culture medium containing 0.3 µg/ml of tetracycline completely inhibits the production of HBV Dane particles. However, when grown in the absence of tetracycline, these cells produce a large number of HBV Dane particles and other HBV replicative intermediates. In the repressed state, the cells do not produce any of the DNA replicative intermediates (i.e. cccDNA, single stranded DNA, relaxed circular DNA, and core DNA); however, in the unrepressed state, all the DNA replicative intermediates are present. Moreover, since the HBV surface antigen contains its own promoter sequences, the Hep AD38 cell line is seropositive for the HBV surface antigen in either the repressed or unrepressed states.

II. Uses of Cell Lines for Cell-Based Assays of Potential Anti-Hepadnaviral Agents The HBV genome-inducible cell lines of the invention may be used in a variety of cell-based assays to evaluate the effectiveness of potential anti-hepadnaviral compounds, utilizing methodologies known in the art. Typical assays are summarized hereinbelow and are described in greater detail in Examples 5–7. These cell-based assays may be performed in standard cell culture media utilizing commonly-available equipment, reagents and culture containers. In the assays summarized below, the day upon which expression of the HBV genome is induced is referred to as "day 0" as a point of reference. Although the exemplary cell line, Hep AD38, is referred to in the methods described below and in the Examples, it will be appreciated by those skilled in the art that other cell lines produced in accordance with the methods of the present invention, will be equally useful in the cell-based assays described.

A. General Cell-Based Assay for Inhibitors of HBV

Three days prior to induction ("day −3") culture plates (e.g., 96-well microtiter plates) are seeded with an appropriate amount of HBV genome-inducible cells per well in a standard cell culture medium containing tetracycline (e.g., 0.3 µg/ml), G418 (e.g., 400 µg/ml), as well as standard concentrations of penicillin, streptomycin and kanamycin or gentamicin to prevent bacterial and mycoplasma contamination. The cells are incubated at 37° C. in a humidified, 5% $CO_2$ incubator. On the day of induction (day 0) wells are washed three times with warm phosphate-buffered saline (PBS). The culture medium is then replaced with fresh medium containing 0.3% dimethylsulfoxide (DMSO), 10% fetal calf serum (FCS), penicillin, streptomycin, kanamycin/gentamicin, containing one of the following ingredients: (1) 0.3 µg/ml tetracycline as a tetracycline control; (2) an equivalent volume of medium instead of tetracycline, as a virus control; (3) various concentrations of a known HBV inhibitor, such as ddC, as a positive control; and (4) various concentrations of one or more of the compounds to be tested. The plates are incubated at 37° C. in humidified, 5% $CO_2$ incubator.

At three days after induction, the medium is removed from each well, and the wells are washed one time with warm PBS. Fresh medium as described above is again added, and plates are again incubated at 37° C. in a humidified, 5% $CO_2$ incubator. This step may be repeated on day 7, 11, etc.

At day four (eight, twelve, etc.) after induction, the medium is removed from the wells and placed into a conical-well 96-well plate. Particulate matter is removed by centrifugation of the plates at, e.g., 2000 rpm for 10 minutes. An aliquot of the supernatant in each well is collected, and either stored at −70° C. or immediately used for detection of HBV DNA.

For detection and quantitation of HBV DNA, viral DNA present in the collected supernatant fluid is denatured with alkali, dot-blotted onto nylon filters, and detected utilizing a radioactive probe specific for HBV DNA sequences. The amount of radioactivity is quantitated with a phosphorimager.

B. Cytotoxicity Assays

A cytotoxicity assay may be conducted to evaluate potential anti-hepadnavirial agents, utilizing a protocol similar to that described above. Instead of measuring HBV DNA, however, cyctoxicity of the various test agents is assessed as follows. On day four after induction, culture medium is removed from the well and cells are washed with PBS. The wells are then treated with a PBS solution containing a mixture of a tetrazolium salt (MTS) and phenazine methosulfate, and the cells are incubated at 37° C. for two hours. Mitochondria of living cells metabolize the tetrazolium dye to produce a color-detectable product. The absorbance at 490 nm is measured in each well, as an indicator of the number of viable cells present in each well.

C. Assays for Intracellular DNA Replicative Intermediates

The cell lines of the present invention may also be utilized to evaluate test compounds for their effect on replication of HBV. This is accomplished by utilizing the general protocols described above, then evaluating cells for the presence of various HBV replicative intermediates, using methods described hereinabove or in greater detail in Example 2.

Such assays include but are not limited to: (1) assays for intracellular core particle DNA; (2) assays for covalently closed circular DNA; (3) assays for relaxed open circular DNA, partially double stranded DNA and single stranded DNA; (4) assays for HBV-specific polyadenylated RNA or pregenomic RNA; (5) assays for Dane particles; and (6) assays for viral proteins.

The following examples are provided to describe the invention in further detail. These examples are intended to illustrate and not to limit the invention.

EXAMPLE 1

Preparation of Hep AD38, An Exemplary Cell Line of the Invention

A. Construction of ptetHBV Plasmid

Plasmids pUHD15-1Neo (encoding the tetR/VP16 transactivator of Gossen & Bujard, 1992, supra) and pUHD10-3 were purchased from Dr. Herman Bujard (Heidelberg, Federal Republic of Germany). Plasmid pCMAYW was constructed by inserting the early promoter of CMV 5' of the human HBV genome such that expression of the genome is under control of the eCMV promoter.

To generate a promoter activated by the tetR/VP16 transactivator, the eukaryotic tetCMV promoter sequence, containing the prokaryotic tetracycline operator (tetO) sequences fused to human cytomegalovirus promoter IE (hCMV), was recovered from pUHD10-3 (Gossen and Bujard, 1992, supra) by polymerase chain reaction (PCR) amplification. The tet operator/eCMV sequence from pUHD10-1 is shown below as Sequence I.D. No. 1, with lower case letters indicating tet operator sequences and upper case letters indicating eCMV sequences.

5'- ttta ccactcccta tcagtgatag agaaaagtga aagtcgagtt taccactccc tatcagtgat agagaaaagt gaaagtcgag tttaccactc cctatcagtg atagagaaaa gtgaaagtcg agtttaccac tcccctatgag tgatagagaa aagtgaaagt cgagtttacc actccctatc agtgatagag aaaagtgaaa gtcgagttta ccactcccta tcagtgatag agaaaagtga agtcgagtt taccactccc tatcagtgat agagaaaagt gaaagtcgag ctcggtaccc gggtcgagTA GGCGTGTACG GTGGGAGGCC TATATAAGCA GAGCTCGTTT AGTGAACCGT CAGATCGCCT GGAGACGCCA TCCACGCTGT TTTGACCTCC ATAGAAGACA CCGGGACCGA TCCAGCCT-3'

The amplified fragment from pUHD10-3 was inserted into the linearized pCMAYW plasmid at the SfiI and BspEI sites. The resulting plasmid, ptetHBV, contains a full length copy of the DNA template encoding the HBV pregenomic RNA under the transcriptional control of the tetCMV promoter.

B. Cotransfection of pUHD15-1Neo and ptetHBV Plasmids in HepG2 cells

HepG2, a human hepatoma-derived cell line was purchased from the American Type Culture Collection (Rockville, Md.). The use of the HepG2 cell line was licensed from the Wistar Institute (Philadelphia, Pa.). Cells were maintained in Delbecco's Modified Eagle's/F-12 (DMEM/F-12), supplemented with 10% fetal bovine serum (FBS), 50 µg/ml penicillin, 50 µg/ml streptomycin, and 100 µg/ml kanamycin (PSK) at 37° C. and 5% carbon dioxide.

For transfection, HepG2 cells were seeded at $4 \times 10^5$ cells/plate on 35 mm plates and incubated at 37° C. to form monolayers. After 24 hours, the cells were cotransfected with pUHD15-1Neo and ptetHBV at a 1:10 ratio, respectively. A total of 3 µg/plate of DNA (0.3 µg of pUHD15-1Neo and 2.7 µg of ptetHBV), were mixed with 15 µl of Transfectase (GIBCO BRL/Life Technologies; Gaithersburg, Md.), diluted to 0.2 ml in OptiMEM Medium (GIBCO BRL) and incubated at room temperature. After 30 minutes, cells were washed twice with OptiMEM medium to remove all fetal bovine serum. The DNA-Transfectace mixture was diluted with 0.8 ml of OptiMEM medium and placed on the cell monolayer. After a 5 hour incubation at 37° C., 1 ml of DMEM/F-12 plus 20% FBS was added and the cells again were incubated at 37° C. The following day, the cells were washed with phosphate buffered saline (PBS) and then reincubated with fresh DMEM/F-12 supplemented with 10% FBS, PSK, and 1 µg/ml tetracycline.

C. Selection of G418 Resistant Clones

Approximately 4 to 7 days after transfection with plasmids pUHD15-1 and ptetHBV, cells were selected for stable transformants by the addition of 400 µg/ml G418 (Geneticin, GIBCO BRL) to the medium. After approximately three weeks, G418 resistant colonies could be distinguished. Individual colonies were picked and seeded into 24 well plates containing DMEM/F-12 plus 10% FBS, PSK, tetracycline (1 µg/ml). Approximately four days later, the medium was removed from each well and replaced with fresh medium containing G418. Upon reaching near confluence, cells were transferred to T25 tissue culture flasks and grown in the presence of G418. A stable transformant of HepG2 was identified. The transformant was named "Hep AD38," and was subjected to more detailed evaluation.

D. Quantitation of Transcriptional Activation of ptetHBV by the Inducible Tet/VP16 Transactivator To assess the inducibility of constructs containing the HBV genome under the control of the tetCMV promoter, T25 flasks containing confluent Hep AD38 cells were split 1:10 into 2 wells of a 24 well plate. Cells were incubated as described in part B above. Upon reaching confluence, cells were washed twice with PBS and incubated with 0.5 ml of medium as described above. Tetracycline was added to only one of the duplicate wells to a final concentration of 1 µg/ml. After four days supernatants were collected, clarified by centrifugation, and stored at −70° C. for further analysis.

Samples were analyzed by dot blot hybridization to detect the presence HBV DNA in the cell culture supernatants (Korba and Milman, 1991, supra). Supernatants were mixed with an equal volume of denaturation solution (1M NaOH/ 10× SSC) and incubated for 20 minutes at room temperature. The denatured supernatant mixture was blotted on a nylon membrane (Amersham, Arlington Heights, Ill.) using a dot blot apparatus (Schleicher and Schuell, Keene, N.H.). Samples were neutralized by washing the membrane with 0.5 ml of 1M Tris, pH 7.2/2M NaCl followed by 0.5 ml of 20× SSC. Filters were then rinsed in 2× SSC, subjected to UV light crosslinking (Stratalinker), and prehybridized in 5× SSC, 5× Denhardt's Reagent, 20 mM NaPO4, pH 6.5, 50% formamide, 1% SDS, and 250 mg/L salmon sperm DNA for 1 hour at 42° C.

A 2.8 Kb fragment corresponding to the HBV sequences of pCMAYW was generated by PCR amplification, and served as a template for the synthesis of [$\alpha$-$^{32}$P]dCTP labelled hybridization probes by random priming according to the vendor's specifications (Megaprime DNA Labelling System, Amersham). Blots were hybridized with the radioactively labelled probe for sixteen hours at 42° C. The filters were then washed twice in 2× SSC/0.1% SDS at 25° C. for 20 minutes each and twice in 0.2× SSC/0.1% SDS at 65° C. for 20 minutes each. Radioactivity for individual samples was quantitated with a Fuji MacBAS 1000 Phosphorimager.

E. Detection of Integrated Vital DNA

Host genomic DNA was isolated from $2.5 \times 10^7$ cells using the Oncor Non-Organic DNA Extraction Kit according to the protocol supplied by the vendor (Oncor, Inc., Gaithersburg, Md.). Approximately 100 μg of genomic DNA from Hep AD38, HepG2 or 2.2.15 cells was digested with Hind III or Pvu II and subjected to electrophoresis on a 0.8% agarose gel in 1× Tris-Acetate-EDTA buffer. The DNA was stained with ethidium bromide (EtBr) and the migration of the DNA in the gel was recorded by photography. The DNA in the gel was simultaneously transferred to two nylon membranes by capillary action, and was fixed to the membranes by UV crosslinking (Stratagens). Integrated HBV DNA was detected on one of the two blots with the HBV-specific radioactively labeled probe described in Example 4. The second blot was probed with actin-specific sequences.

Results are shown in FIG. 1. FIG. 1A shows the Hind III digestion of the genomic DNA of HepG2, 2.2.15 and Hep AD38 cell lines, while FIG. 1B shows the Pvu II digestion. As can be seen, the presence of one band (peak) in the Hep AD38 cell lines in both digestions shows that the genome of the Hep AD38 cell line contains only one copy of the HBV genomic sequence, whereas the HepG2 cell line contains no copies, and the HepG2 2.2.15 cell line contains multiple copies of the HBV genome.

EXAMPLE 2

Preparation of Vital Replicative Intermediates

A. Covalently Closed Circular Vital DNA (cccDNA)

For each of the Hep AD38, HepG2 and 2.2.15 cell lines, two 60 mm plates were seeded with $3 \times 10^6$ cells and allowed to grow as described above. When the cells became confluent, the medium was changed and tetracycline was removed from the medium on one of the plates. After a six day induction period, the medium again was removed and the cells were washed with PBS. Cells were then incubated at 37° C. for 10 minutes with 1 ml lysis buffer (0.5% SDS, 10 mM Tris-HCl, pH 7.5, 10 mM EDTA, 0.15M NaCl). The cell solutions were transferred to 1.5 ml Eppendorf tubes, adjusted to 0.5 M KCl, and incubated on ice for 15 minutes. The lysates were then clarified by high-speed centrifugation for 15 minutes at 4° C., and the supernatants were collected. DNA was isolated from the supernatants by phenol extraction followed by cold ethanol precipitation. Pelleted DNA was resuspended in 40 μl TE buffer.

B. Vital Core DNA

For each cell line, two 60 mm plates were seeded with $3 \times 10^6$ cells. When the cells reached full confluency, the medium was changed and tetracycline was removed from the medium of one of the plates. After a 7 day induction period, the medium was removed and cells were washed with PBS. Cells were lysed by the addition of 0.6 ml of transfection lysis buffer (50 mM Tris, pH 8.0, 1 mM EDTA, 1% NP40) to each plate. The mixture was pipetted thoroughly to ensure complete cell lysis. The lysate was then transferred to a 1.5 ml Eppendorf tube and centrifuged at high speed for 1 minute. The supernatant was extracted, adjusted to 10 mM magnesium acetate, 100 μg/ml DNase I, and 100 μg/ml RNase A, and incubated at 37° C. for 30 minutes. Following incubation, immature virions were precipitated by adding 16 ul of 0.5M EDTA (pH 8.0) and 130 μl of 35% PEG-8000 in 1.75M NaCl and incubating at 4° C. After one hour, the solution was centrifuged at 2,000 RPM for 4 minutes and the pellet resuspended in 300 μl TNE, 8 ul 20% SDS, and 10 μl proteinase K (20 mg/ml). Following a 1 hour incubation at 45° C., the DNA was extracted 3 times with phenol, precipitated with 1 μg of yeast tRNA, ⅙ volume 10M LiCl and 2.2 volumes ice cold ethanol. The final pellet was resuspended in 15 μl TE buffer.

C. Other Replicative Intermediates

Other replicative intermediates were collected from the pellets remaining from the high-speed centrifugation described in Section A above (preparation of cccDNA). Pellets were resuspended in 1 ml of Tris-EDTA buffer containing 0.5 mg/ml Proteinase K, incubated at 45° C. for 90 minutes, then phenol extracted twice. DNA was precipitated with ETOH and resuspended in 40 μl of Tris-EDTA buffer.

D. Gel Electrophoresis and Southern Blotting Analysis of Replicative Intermediates Fifteen microliters of each of the vital core DNA preparations, 20 μL of the cccDNA preparations and 20 μl of the "other replicative intermediates" preparation were electrophoresed on a 1.5% agarose gel in Tris-Acetate-EDTA buffer. The EtBr-stained DNA in the gel was visualized by U.V. light and photographed. The DNA was then transferred to a nylon membrane and crosslinked to the membrane by UV light. Radioactively labelled probes specific for HBV DNA sequences were used to detect viral DNA by conventional Southern blot techniques.

Figure 3:
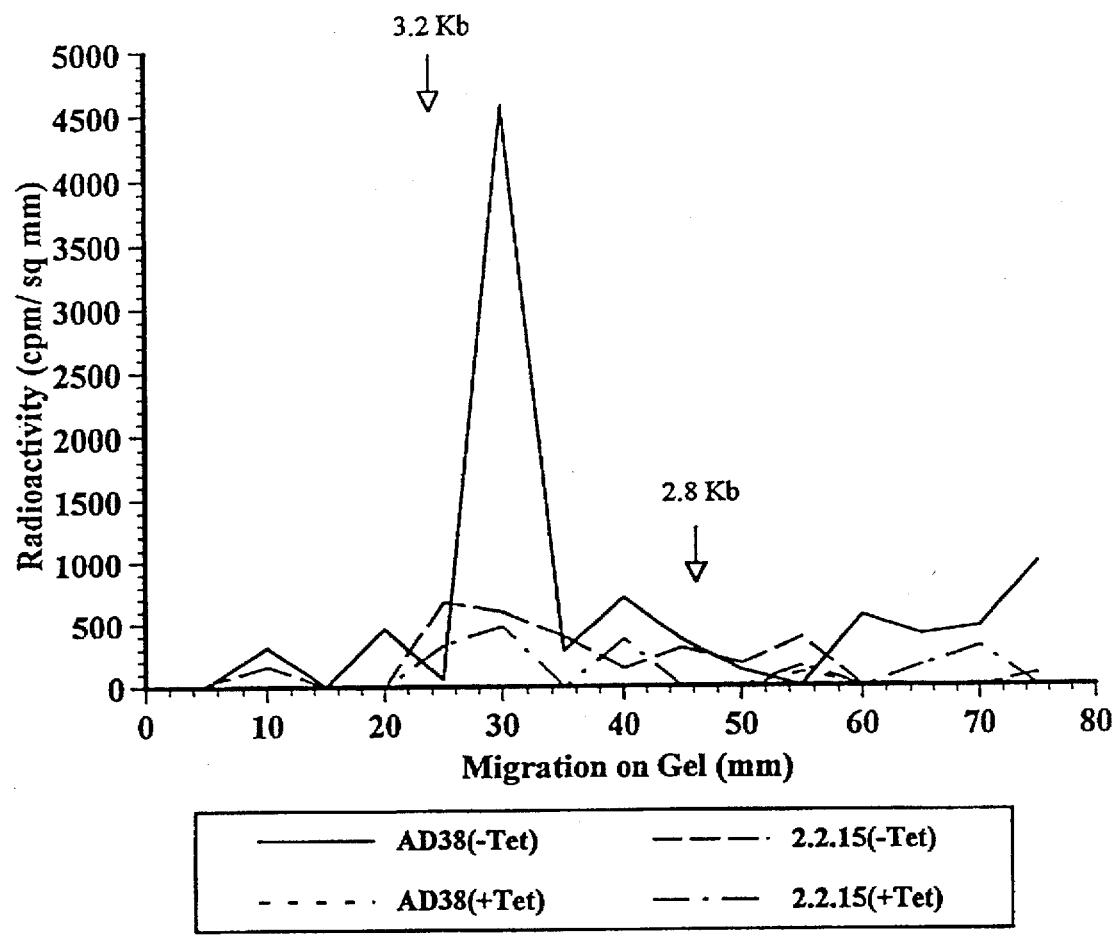
FIG. 3. Analysis of cells for HBV replicative intermediates. DNA from Hep AD38 (induced or uninduced) and 2.2.15 cells (induced or uninduced) were separated by electrophoresis on a 1% agarose gel and probed for the presence of the HBV genome sequences with a radioactively labeled probe.
Figure 4:
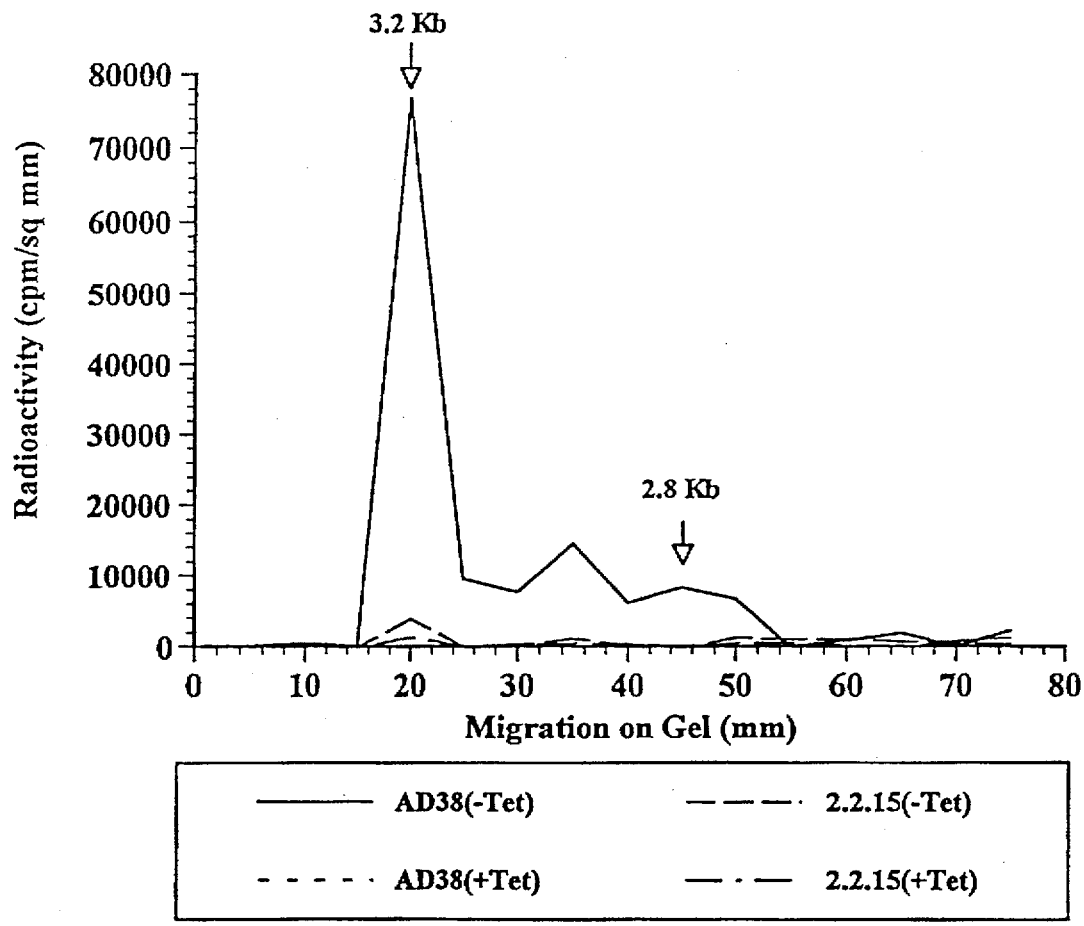
FIG. 4. Analysis of cells for HBV core DNA. DNA from Hep AD38 (induced or uninduced) and 2.2.15 cells (induced or uninduced) were separated by electrophoresis on a 1% agarose gel and probed for the presence of the HBV genome sequences with a radioactively labeled probe.

Results are shown in FIGS. 2, 3 and 4. FIG. 2 shows the results of the analysis of Hep AD38 cells and 2.2.15 cells in the presence or absence of tetracycline, for production of covalently closed circular DNA. FIG. 3 shows a similar analysis for the presence and quantity of HBV replicative intermediates. FIG. 4 shows a similar analysis for the presence and quantity of HBV core DNA. In each of the Figures, it can be seen that Hep AD38 cells, in the absence of tetracycline (i.e., induced), make the appropriate DNA intermediates during the expression of the HBV genome by the tet operator-CMV promoter, and that these intermediates are not made when the cells are grown in the presence of tetracycline. The inclusion of the 2.2.15 cells demonstrate that expression of the HBV intermediates in the Hep AD38 cell line is much greater than in the 2.2.15 cell line, as well as being inducible. The sizes of the intermediates are indicated on the Figures, and are in agreement with those published for 2.2.15 cells. In FIG. 3, the largest peak represents partially double stranded viral DNA, while the smaller peak to the right of the large peak is likely single stranded viral DNA.

EXAMPLE 3

Preparation and Analysis of Dane Particles

For each cell line, two 60 mm plates were seeded with $3 \times 10^6$ cells. When the cells reached full confluency, the medium was changed and tetracycline was removed from the medium of one the plates. After a 7 day induction period, the medium was collected and clarified by low speed centrifugation. The medium was adjusted to 10% glycerol (by volume) and incubated one hour at 4° C. Dane particles were pelleted by low speed centrifugation and resuspended in PBS. The viral capsid was disrupted with 1% NP-40 (Sigma Chemical Co., St Louis, Mo.) and the capsid proteins were digested with proteinase K (50 μg/ml). The viral DNA was analyzed by dot blot hybridization using a radioactively labeled probe specific for HBV DNA. Results are shown in Table 1.

TABLE 1

Induction of HBV Dane particles.

| Cell Lines | HBV DNA (CPM/well) | | | |
|---|---|---|---|---|
| | Day 4 | | Day 7 | |
| | +Tet. | −Tet. | +Tet | −Tet |
| HepG2 | 0 | 0 | 0 | 0 |
| 2.2.15 | $4 \times 10^3$ | $4.1 \times 10^3$ | $1.8 \times 10^4$ | $1.1 \times 10^4$ |
| Hep AD38 | 0 | $2.3 \times 10^4$ | 0 | $2.3 \times 10^5$ |

As can be seen in Table 1, Hep AD38 cells grown in the presence of tetracycline do not release HBV DNA into the extracellular environment. However, in the absence of tetracycline, the Hep AD38 cells excrete high levels of HBV DNA into the extracellular medium. The control cell line (2.2.15) showed no response to the presence or absence of tetracycline with regard to release of HBV DNA into the medium. The parental cell line, HepG2, does not release HBV DNA into the extracellular environment under either condition.

EXAMPLE 4

Susceptibility of Inducibly Expressed HBV to Known HBV Inhibitors

Cells were seeded in 24 well plates at $4 \times 10^5$ cells/well and were grown to 100% confluency (approximately 3 days). At this time (day 0), cells were washed 3 times with PBS and 0.5 ml of medium containing various concentrations of known HBV inhibitors (ddC, 3TC and CDG). For each compound, four different concentrations and a negative control were tested, in the presence or in the absence of tetracycline. Typically, the medium was replaced 24 hours prior to collection with samples being collected four, eight, and twelve days after induction. Media were clarified by centrifugation and stored at −70° C. for further analysis. The procedure for susceptibility testing in a 96-well format was essentially the same as for the 24 well plate format except that cells were seeded in 96 well plates at $5 \times 10^4$ cells/well, 5 concentrations of drug were tested, and the volume of medium used was 100 µl. In addition, samples were removed from the wells for HBV DNA determination either with and without medium changes 24 hours prior to collection.

The samples were evaluated to determine the effective concentration of the inhibitors that inhibited the release of HBV DNA by 50%. This value is referred to as the $EC_{50}$ for the compound. Table 2 shows the $EC_{50}$ values of the three selected known anti-hepadnaviral compounds. As can be seen from Table 2, the $EC_{50}$ values determined in the inducible Hep AD38 cell line were equivalent to those determined in the 2.2.15 cell line, indicating that the Hep AD38 cells were equally as effective in establishing an $EC_{50}$ value for a known compound. Moreover, the Hep AD38 assay was performed in significantly less time.

TABLE 2

Inhibition of the release of HBV DNA into the extracellular environment.

| Cell Lines | $EC_{50}$ OF SELECTED COMPOUNDS | | |
|---|---|---|---|
| | 3TC | ddC | CDG |
| 2.2.15 | 0.05 µM | 6 µM | 19 nM |
| Hep Ad38 | 0.02 µM | 8 µM | 11 nM |

EXAMPLE 5

Hep AD38 Model Cell-Based Assay for Inhibitors of HBV

A. Day −3:

1. 96-well plates are seeded with $6 \times 10^4$ Hep AD38 cells/well in 100 µls F-12/DMEM medium containing 10% fetal calf serum (FCS), tetracycline (0.3 µg/ml), G418(400 µg/ml), penicillin, streptomycin, and either kanamycin or gentamicin, and incubated at 37° C. in a humidified 5% $CO_2$ incubator.

B. Day 0:

1. Wash wells three times with warm PBS.
2. Replace medium with
   a. 100 µl fresh medium containing 0.3% DMSO, 10% FCS, penicillin, streptomycin, kanamycin/gentamicin, and tetracycline (0.3 µg/ml) as a tetracycline control (wells on the outside edge of each plate).
   b. 100 µl fresh medium containing 0.3% DMSO, 10% FCS, penicillin, streptomycin, and kanamycin/gentamicin as a virus control.
   c. 100 µl fresh medium containing 0.3% DMSO, 10% FCS, penicillin, streptomycin, kanamycin/gentamicin, and either 100, 20, 10, 3, 1 µM ddC as a positive control.
   d. 100 µl fresh medium containing 0.3% DMSO, 10% FCS, penicillin, streptomycin, kanamycin/gentamicin, and 3TC (0.3 µM) as a positive control.
   e. 100 µl fresh medium containing 0.3% DMSO, 10% FCS, penicillin, streptomycin, kanamycin/gentamicin, and desired concentration(s) of test compound.
3. Incubate plates at 37° C. in a humidified, 5% $CO_2$ incubator.

C. Day 3:

1. Remove medium from each well, and wash cells one time with warm PBS and add fresh medium as stated in Step B2.a.–e, and incubate plates at 37° C. in a humidified, 5% $CO_2$ incubator.

D. Day 4:

1. Remove the medium from the wells and place into conical well 96-well plates.
2. Remove particulate matter by centrifugation of plates at 2000 RPM for 10 minutes.
3. Collect 90 µl of supernatant into 96-well plates and either store −70° C. or immediately continue with the detection procedure.

E. Detection of HBV DNA:

1. Denature viral DNA with alkali, dot blot DNA onto nylon filter, and detect presence of HBV DNA with a radioactive probe specific for HBV. Quantitate amount of radioactivity with a phosphorimager.

EXAMPLE 6

Model Cytotoxicity Assay Using Hep AD38 Cells

A. Day-3:

1. 96-well plates are seeded with $6\times10^4$ Hep AD38 cells/well in 100 μls F-12/DMEM medium containing 10% fetal calf serum (FCS), tetracycline (0.3 μg/ml), G418 (400 μg/ml), penicillin, streptomycin, and either kanamycin or gentamicin, and incubate at 37° C. in a humidified 5% $CO_2$ incubator.

B. Day 0:
1. Wash wells three time with warm PBS.
2. Replace medium with
   a. 100 μl fresh medium containing 0.3% DMSO, 10% FCS, penicillin, streptomycin, kanamycin/gentamicin and tetracycline (0.3 μg/ml) as a tetracycline control (wells on the outside edge of each plate).
   b. 100 μl fresh medium containing 0.3% DMSO, 10% FCS, penicillin, streptomycin, and kanamycin/gentamicin in two columns as a control for zero toxicity.
   c. 100 μl fresh medium containing 0.3% DMSO, 10% FCS, penicillin, streptomycin, kanamycin/gentamicin, and desired concentration(s) of test compound.
3. Incubate plates at 37° C. in a humidified, 5% $CO_2$ incubator.

C. Day 4:
1. Remove medium from cells and wash with PBS.
2. Add 100 μl of PBS and 20 μl of a tetrazolium salt (MTS) and phenazine methosulfate mixture. Incubate at 37° C. for two hours.
3. Read the absorbance for each well at 490 nm.

EXAMPLE 7

Model Assay for Intracellular DNA Replicative Intermediates Using Hep AD38 Cells A. Expression of intracellular DNA replicative intermediates:

1. 35 mm plates are seeded with $3\times10^5$ Hep AD38 cells in 2 mls of F-12/DMEM medium containing 10% fetal calf serum (FCS), tetracycline (0.3 μg/ml), G418 (400 μg/ml), penicillin, streptomycin, and either kanamycin or gentamicin, and incubate overnight at 37° C. in a humidified, 5% $CO_2$ incubator.

2. Wash cells three times with warm PBS and add 2 mls of F-12/DMEM medium containing 10% fetal calf serum (FCS), penicillin, streptomycin, either kanamycin or gentamicin, and the desired concentration of experimental compound. Cells are incubated at 37° C. in a humidified 5% $CO_2$ incubator.

3. Assay for DNA intermediates as follows:

B. Assay for intracellular core particle DNA:

Seven days after the removal of tetracycline from the medium, the cells are lysed and intracellular core particle DNA is isolated as described in previous Examples. Quantitation of the amount of radioactivity found on the nylon membrane is performed with a phosphorimager.

C. Assay for cccDNA:

Six days after the removal of tetracycline from the medium the cells were lysed and cccDNA is isolated as described in previous Examples. Quantitation of the amount of radioactivity found on the nylon membrane is performed with a phosphorimager.

D. Assay for HBV-specific polyadenylated RNA:

Six days after the removal of tetracycline from the medium, the total cellular RNA is isolated by the guanidinium thiocyanate procedure (Chirgwin, et al., Biochem. 18:5294–5299, 1974). Polyadenylated RNA is separated from the remaining RNA with oligo(dT)-Sepharose. This RNA is separated by size in a 1% agarose gel containing formaldehyde and then blotted onto a nylon filter. HBV specific RNA is detected with a radioactively labeled DNA probe specific for HBV.

While certain preferred embodiments of the present invention have been described and specifically exemplified above, it is not intended that the invention be limited to such embodiments. Various modifications may be made thereto within the scope and spirit of the present invention, as set forth in the following claims.

---

What is claimed is:

1. A cell line capable of inducibly expressing a genome of hepatitis B virus, said cell line being stably transformed with:
   a) a single copy of a cDNA encoding hepatitis B virus pregenomic RNA, said cDNA being operably linked to a target nucleotide sequence for activating expression of said hepatitis B virus genome, said activation of expression being caused by interaction of said target sequence with a transactivator protein that specifically interacts with said target sequence; and
   b) a gene encoding and expressing said transactivator protein, said transactivator protein being responsive to induction under pre-determined inducing conditions, said induction enabling said transactivator protein to interact with said target nucleotide sequence, said interaction thereby activating expression of said hepatitis B virus genome.

2. The cell line of claim 1, which is a human cell line.

3. The cell line of claim 2, which is a hepatic cell line.

4. The cell line of claim 3, which is a derivative of HepG2.

5. The cell line of claim 1, wherein the hepatitis B virus genome is a human hepatitis B virus genome.

6. The cell line of claim 1, wherein the transactivator protein is a tetR/VP16 chimeric protein and the target sequence comprises at least one tet operator operatively linked to a minimal promoter.

7. The cell line of claim 6, wherein said minimal promoter is a cytomegalovirus early promoter.

8. The cell line of claim 6, wherein said target sequence comprises Sequence I.D. No. 1.

9. The cell line of claim 6, wherein the transactivator protein is induced by removal of tetracycline from culture medium in which the cell line is maintained.

10. The cell line of claim 1, which is a human hepatic cell line transformed with a gene encoding a tetR/VP16 transactivator protein and a human hepatitis B virus genome operably linked to a target sequence comprising at least one tet operator and a minimal promoter, said hepatitis B virus genome remaining non-expressed when said cell line is maintained in the presence of tetracycline, said hepatitis B virus genome being inducibly expressed upon removal of said tetracycline from the presence of said cell line.

11. The cell line of claim 10, having the identifying characteristics of Hep AD38 (ATCC CRL 12077).

12. A human hepatic cell line that inducibly expresses a genome of human hepatitis B virus, said cell line being stably transformed with:
   a) a single copy of a cDNA encoding hepatitis B virus pregenomic RNA, said cDNA being operably linked to a target nucleotide sequence for activating expression of said hepatitis B virus genome, said target sequence comprising at least one tet operator operably disposed in the 5' direction from a minimal promoter, said activation of expression being caused by interaction of said target sequence with a transactivator protein that specifically interacts with said target sequence; and
   b) a gene encoding and expressing said transactivator protein, said transactivator protein comprising a tetR/VP16 chimeric protein, said transactivator protein being responsive to induction under inducing conditions comprising removal of tetracycline from culture media in which said cell line is maintained, said induction enabling said transactivator protein to interact with said target nucleotide sequence, said interaction thereby activating expression of said hepatitis B virus genome.

13. The cell line of claim 12, having the identifying characteristics of Hep AD38 (ATCC CRL 12077).

14. A method of inducibly expressing a hepatitis B virus genome in a cultured mammalian cell line stably transformed with a construct encoding said genome, said method comprising:
   a) providing said cell line stably transformed with said construct encoding a single cDNA copy of hepatitis B virus pregenomic RNA, said cDNA being operably linked to a target nucleotide sequence for activating expression of said hepatitis B virus genome, said activation of expression being caused by interaction of said target sequence with a transactivator protein that specifically interacts with said target sequence, said cell line also being stably transformed with a gene encoding and expressing said transactivator protein;
   b) culturing said cell line in a nutrient medium under non-inducing conditions in which said transactivator protein is substantially prevented from interacting with said target nucleotide sequence;
   c) placing said cell line under inducing conditions that enable said transactivator protein to interact with said target nucleotide sequence, thereby activating expression of said hepatitis B virus genome; and
   d) maintaining said cell line under said inducing conditions for a pre-determined time to allow accumulation of products of expression of said hepatitis B virus genome.

15. The method of claim 14, wherein said cell line has the identifying characteristics of Hep AD38 (ATCC CRL 12077).

16. The method of claim 15, wherein said non-inducing conditions comprise said nutrient medium that contains at least about 0.3 µg/ml tetracycline and said inducing conditions comprise a nutrient medium containing from zero to about 0.03 µg/ml tetracycline.

17. The method of claim 14, which further comprises the step of detecting the presence or quantity of at least one of said hepatitis B virus genome expression products.

18. The method of claim 17, wherein said at least one of said hepatitis B virus genome expression products is selected from the group consisting of: Dane particles, viral core DNA, covalently closed circular viral DNA, relaxed circular viral DNA, partially double stranded viral DNA, single stranded viral DNA, viral pregenomic RNA, viral messenger RNA, and viral proteins.

19. A cell-based assay for screening potential anti-hepadnaviral agents, said assay comprising the steps of:

a) providing a cultured cell line stably transformed with a single cDNA copy of hepatitis B virus pregenomic RNA, said cDNA being operably linked to a target nucleotide sequence for inducibly activating expression of said hepatitis B virus genome, said activation of expression being caused by interaction of said target sequence with an inducible transactivator protein that specifically interacts with said target sequence, said cell line also being stably transformed with a gene encoding and expressing said transactivator protein;

b) establishing at least one control sample and at least one test sample, each said sample comprising a substantially equivalent number of cells from said cultured cell line, in a substantially equivalent volume of culture fluid;

c) exposing said test sample to said potential anti-hepadnaviral agent;

d) culturing said cell lines comprising each said control sample and test sample in a nutrient medium under non-inducing conditions in which said transactivator protein is substantially prevented from interacting with said target nucleotide sequence;

e) placing said cell lines comprising each said control sample and test sample under inducing conditions that enable said transactivator protein to interact with said target nucleotide sequence, thereby activating expression of said hepatitis B virus genome;

f) detecting in each said control sample and test sample the presence or quantity of at least one hepatitis B virus expression product accumulated in said sample as a result of expression of said hepatitis B virus genome; and g) comparing the presence or quantity of said at least one expression product in said control sample and said test sample, a difference between said control sample and said test sample being attributable to exposure of said test sample to said potential anti-hepadnaviral agent.

20. The method of claim 19, wherein said cell line has the identifying characteristics of Hep AD38 (ATCC CRL 12077).

21. The method of claim 20, wherein said non-inducing conditions comprise said nutrient medium that contains at least about 0.3 µg/ml tetracycline and said inducing conditions comprise a nutrient medium containing from zero to about 0.03 µg/ml tetracycline.

22. The method of claim 18, wherein said at least one of said hepatitis B virus genome expression products is selected from the group consisting of: Dane particles, viral core DNA, covalently closed circular viral DNA, relaxed circular viral DNA, partially double stranded viral DNA, single stranded viral DNA, viral pregenomic RNA, viral messenger RNA, and viral proteins.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 432 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

```
TTTACCACTC  CCTATCAGTG  ATAGAGAAAA  GTGAAAGTCG  AGTTTACCAC  TCCCTATCAG      60

TGATAGAGAA  AAGTGAAAGT  CGAGTTTACC  ACTCCCTATC  AGTGATAGAG  AAAAGTGAAA     120
```

| | | | | | |
|---|---|---|---|---|---|
| GTCGAGTTTA | CCACTCCCTA | TGAGTGATAG | AGAAAAGTGA | AAGTCGAGTT | TACCACTCCC | 180 |
| TATCAGTGAT | AGAGAAAAGT | GAAAGTCGAG | TTTACCACTC | CCTATCAGTG | ATAGAGAAAA | 240 |
| GTGAAAGTCG | AGTTACCAC | TCCCTATCAG | TGATAGAGAA | AAGTGAAAGT | CGAGCTCGGT | 300 |
| ACCCGGGTCG | AGTAGGCGTG | TACGGTGGGA | GGCCTATATA | AGCAGAGCTC | GTTTAGTGAA | 360 |
| CCGTCAGATC | GCCTGGAGAC | GCCATCCACG | CTGTTTTGAC | CTCCATAGAA | GACACCGGGA | 420 |
| CCGATCCAGC | CT | | | | | 432 |